United States Patent
Williams

(10) Patent No.: US 11,642,131 B2
(45) Date of Patent: May 9, 2023

(54) DEVICES AND METHODS FOR SHORTENING A RECTAL STUMP DURING A LOWER ANTERIOR RESECTION PROCEDURE

(71) Applicant: Covidien LP, Mansfield, MA (US)

(72) Inventor: Justin Williams, Southbury, CT (US)

(73) Assignee: Covidien LP, Mansfield, MA (US)

( * ) Notice: Subject to any disclaimer, the term of this patent is extended or adjusted under 35 U.S.C. 154(b) by 8 days.

(21) Appl. No.: 17/321,622

(22) Filed: May 17, 2021

(65) Prior Publication Data

US 2022/0361881 A1    Nov. 17, 2022

(51) Int. Cl.
| | | |
|---|---|---|
| *A61B 17/064* | (2006.01) | |
| *A61B 17/11* | (2006.01) | |
| *A61B 17/115* | (2006.01) | |
| *A61B 17/34* | (2006.01) | |

(52) U.S. Cl.
CPC ....... *A61B 17/1114* (2013.01); *A61B 17/1155* (2013.01); *A61B 17/3496* (2013.01)

(58) Field of Classification Search
CPC .................. A61B 17/1114; A61B 17/1155
See application file for complete search history.

(56) References Cited

U.S. PATENT DOCUMENTS

| | | |
|---|---|---|
| 3,193,165 A | 7/1965 | Akhalaya et al. |
| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |

(Continued)

FOREIGN PATENT DOCUMENTS

| | | |
|---|---|---|
| CA | 908529 A | 8/1972 |
| CA | 2805365 A1 | 8/2013 |

(Continued)

OTHER PUBLICATIONS

Extended European Search Report from Appl. No. 14181908.6 dated May 26, 2015.

(Continued)

*Primary Examiner* — Eyamindae C Jallow
(74) *Attorney, Agent, or Firm* — Carter, DeLuca & Farrell, LLP

(57) ABSTRACT

A loading unit for a circular stapling device includes a shell member, a staple pusher assembly operably disposed within the shell member, a knife pusher assembly operably disposed within the shell member, a trocar assembly operably disposed within the shell member, and a tissue retraction assembly disposed within the shell member between the knife pusher assembly and the trocar assembly. The shell member includes an elongate tubular portion. The trocar assembly includes a trocar member movable from an advance position and a retracted position. The tissue retraction assembly includes a tissue retractor.

19 Claims, 13 Drawing Sheets

(56) References Cited

U.S. PATENT DOCUMENTS

| | | |
|---|---|---|
| 4,379,457 A | 4/1983 | Gravener et al. |
| 4,473,077 A | 9/1984 | Noiles et al. |
| 4,476,863 A | 10/1984 | Kanshln et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,144 A | 11/1995 | Guy et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Billner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |

(56) References Cited

U.S. PATENT DOCUMENTS

| | | |
|---|---|---|
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |

(56) References Cited

U.S. PATENT DOCUMENTS

| | | |
|---|---|---|
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,479,968 B2 | 7/2013 | Hodgkinson et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 * | 11/2013 | Hartwick .......... A61B 17/00234 606/139 |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,627,995 B2 | 1/2014 | Smith et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,646,674 B2 | 2/2014 | Schulte et al. |
| 8,662,370 B2 | 3/2014 | Takei |
| 8,663,258 B2 | 3/2014 | Bettuchi et al. |
| 8,672,207 B2 | 3/2014 | Shelton, IV et al. |
| 8,672,931 B2 | 3/2014 | Goldboss et al. |
| 8,672,951 B2 | 3/2014 | Smith et al. |
| 8,678,264 B2 | 3/2014 | Racenet et al. |
| 8,679,137 B2 | 3/2014 | Bauman et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,695,864 B1 | 4/2014 | Hausen |
| 8,708,212 B2 | 4/2014 | Williams |
| 8,733,611 B2 | 5/2014 | Milliman |
| 8,733,615 B2 | 5/2014 | Nalagatla et al. |
| 8,746,531 B2 | 6/2014 | Wenchell et al. |
| 8,746,532 B2 | 6/2014 | Nalagatla et al. |
| 8,783,543 B2 | 7/2014 | Shelton, IV et al. |
| 8,789,737 B2 | 7/2014 | Hodgkinson et al. |
| 8,800,838 B2 | 8/2014 | Shelton, IV |
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,821,523 B2 | 9/2014 | Heinrich et al. |
| 8,827,903 B2 | 9/2014 | Shelton, IV et al. |
| 8,833,629 B2 | 9/2014 | Nalagatla et al. |
| 8,840,004 B2 | 9/2014 | Holsten et al. |
| 8,844,792 B2 | 9/2014 | Viola |
| 8,845,661 B2 | 9/2014 | D'Arcangelo et al. |
| 8,870,911 B2 | 10/2014 | Williams et al. |
| 8,875,974 B2 | 11/2014 | Rebuffat et al. |
| 8,893,948 B2 | 11/2014 | Williams |
| 8,910,847 B2 | 12/2014 | Nalagatla et al. |
| 8,925,785 B2 | 1/2015 | Holsten et al. |
| 8,925,786 B2 | 1/2015 | Holsten et al. |
| 8,967,448 B2 | 3/2015 | Carter et al. |
| 8,978,955 B2 | 3/2015 | Aronhalt et al. |
| 9,010,608 B2 | 4/2015 | Casasanta, Jr. et al. |
| 9,010,612 B2 | 4/2015 | Stevenson et al. |
| 9,016,540 B2 | 4/2015 | Whitman et al. |
| 9,033,204 B2 | 5/2015 | Shelton, IV et al. |
| 9,095,340 B2 | 8/2015 | Felder et al. |
| 9,113,871 B2 | 8/2015 | Milliman et al. |
| 9,113,877 B1 | 8/2015 | Whitman et al. |
| 9,113,883 B2 | 8/2015 | Aronhalt et al. |
| 9,113,884 B2 | 8/2015 | Shelton, IV et al. |
| 9,113,885 B2 | 8/2015 | Hodgkinson et al. |
| 9,125,654 B2 | 9/2015 | Aronhalt et al. |
| 9,155,536 B1 | 10/2015 | Hausen et al. |
| 9,161,757 B2 | 10/2015 | Bettuchi |
| 9,204,881 B2 | 12/2015 | Penna |
| 9,211,122 B2 | 12/2015 | Hagerty et al. |
| 9,220,504 B2 | 12/2015 | Viola et al. |
| 9,232,941 B2 | 1/2016 | Mandakolathur Vasudevan et al. |
| 9,232,945 B2 | 1/2016 | Zingman |
| 9,289,207 B2 | 3/2016 | Shelton, IV |
| 9,301,763 B2 | 4/2016 | Qiao et al. |
| 9,307,994 B2 | 4/2016 | Gresham et al. |
| 9,326,773 B2 | 5/2016 | Casasanta, Jr. et al. |
| 9,351,729 B2 | 5/2016 | Orban, III et al. |
| 9,351,731 B2 | 5/2016 | Carter et al. |
| 9,364,229 B2 | 6/2016 | D'Agostino et al. |
| 9,370,366 B2 | 6/2016 | Mozdzierz |
| 9,370,367 B2 | 6/2016 | Mozdzierz |

(56) References Cited

U.S. PATENT DOCUMENTS

| | | |
|---|---|---|
| 9,393,014 B2 | 7/2016 | Milliman |
| 9,408,603 B2 | 8/2016 | Patel |
| 9,421,013 B2 | 8/2016 | Patel et al. |
| 9,445,817 B2 | 9/2016 | Bettuchi |
| 9,451,962 B2 | 9/2016 | Olson |
| 9,456,821 B2 | 10/2016 | Bettuchi et al. |
| 9,463,022 B2 | 10/2016 | Swayze et al. |
| 9,492,166 B2 | 11/2016 | Kostrzewski |
| 9,498,222 B2 | 11/2016 | Scheib et al. |
| 9,504,470 B2 | 11/2016 | Milliman |
| 9,522,005 B2 | 12/2016 | Williams et al. |
| 9,549,738 B2 | 1/2017 | Mandakolathur Vasudevan et al. |
| 9,572,572 B2 | 2/2017 | Williams |
| 9,579,102 B2 | 2/2017 | Holsten et al. |
| 9,592,055 B2 | 3/2017 | Milliman et al. |
| 9,592,056 B2 | 3/2017 | Mozdzierz et al. |
| 9,597,081 B2 | 3/2017 | Swayze et al. |
| 9,597,082 B2 | 3/2017 | Stokes et al. |
| 9,603,599 B2 | 3/2017 | Miller et al. |
| 9,629,624 B2 | 4/2017 | Hessler et al. |
| 9,636,112 B2 | 5/2017 | Penna et al. |
| 9,649,110 B2 | 5/2017 | Parihar et al. |
| 9,649,113 B2 | 5/2017 | Ma et al. |
| 9,668,740 B2 | 6/2017 | Williams |
| 9,675,348 B2 | 6/2017 | Smith et al. |
| 9,681,872 B2 | 6/2017 | Jankowski et al. |
| 9,681,873 B2 | 6/2017 | Smith et al. |
| 9,687,234 B2 | 6/2017 | Smith et al. |
| 9,693,773 B2 | 7/2017 | Williams |
| 9,700,309 B2 | 7/2017 | Jaworek |
| 9,706,999 B2 | 7/2017 | Motai |
| 9,713,469 B2 | 7/2017 | Leimbach et al. |
| 9,737,304 B2 | 8/2017 | Bettuchi et al. |
| 9,743,955 B2 | 8/2017 | Hill et al. |
| 9,750,503 B2 | 9/2017 | Milliman |
| 9,763,663 B2 | 9/2017 | Weisshaupt et al. |
| 9,801,626 B2 | 10/2017 | Parihar et al. |
| 9,833,235 B2 | 12/2017 | Penna et al. |
| 9,844,368 B2 | 12/2017 | Boudreaux et al. |
| 9,861,368 B2 | 1/2018 | Racenet et al. |
| 9,883,862 B2 | 2/2018 | Rebuffat et al. |
| 9,907,600 B2 | 3/2018 | Stulen et al. |
| 10,039,549 B2 | 8/2018 | Williams |
| 10,085,744 B2 | 10/2018 | Williams et al. |
| 10,105,137 B2 | 10/2018 | Holsten et al. |
| 10,117,655 B2 | 11/2018 | Scirica et al. |
| 10,117,656 B2 | 11/2018 | Sgroi, Jr. |
| 10,136,888 B2 | 11/2018 | Chen et al. |
| 10,149,680 B2 | 12/2018 | Parihar et al. |
| 10,154,845 B2 | 12/2018 | Williams |
| 10,172,622 B2 | 1/2019 | Kelley |
| 10,178,994 B2 | 1/2019 | Lee et al. |
| 10,188,386 B2 | 1/2019 | Measamer et al. |
| 10,190,888 B2 | 1/2019 | Hryb et al. |
| 10,194,911 B2 | 2/2019 | Miller et al. |
| 10,226,253 B2 | 3/2019 | DiNardo et al. |
| 10,245,038 B2 | 4/2019 | Hopkins et al. |
| 10,271,842 B2 | 4/2019 | Fox et al. |
| 10,271,843 B2 | 4/2019 | Shi et al. |
| 10,307,157 B2 | 6/2019 | Miller et al. |
| 10,321,908 B2 | 6/2019 | Carter et al. |
| 10,327,779 B2 | 6/2019 | Richard et al. |
| 10,342,629 B2 | 7/2019 | Penna et al. |
| 10,405,855 B2 | 9/2019 | Stager et al. |
| 10,413,299 B2 | 9/2019 | Milliman |
| 10,426,468 B2 | 10/2019 | Contini et al. |
| 10,426,480 B2 | 10/2019 | Scirica et al. |
| 10,433,848 B2 | 10/2019 | Chen et al. |
| 10,456,134 B2 | 10/2019 | DiNardo et al. |
| 10,463,365 B2 | 11/2019 | Williams |
| 10,463,373 B2 | 11/2019 | Mozdzierz et al. |
| 10,463,374 B2 | 11/2019 | Sgroi, Jr. |
| 10,470,770 B2 | 11/2019 | Shelton, IV et al. |
| 10,470,771 B2 | 11/2019 | D'Agostino et al. |
| 10,499,909 B2 * | 12/2019 | Scheib ................ A61B 17/0482 |
| 10,499,922 B2 | 12/2019 | Sgroi, Jr. |
| 10,506,920 B2 | 12/2019 | Hasser et al. |
| 10,507,039 B2 | 12/2019 | Williams |
| 10,512,467 B2 | 12/2019 | Swayze et al. |
| 10,524,795 B2 | 1/2020 | Nalagatla et al. |
| 10,524,798 B2 | 1/2020 | Williams |
| 10,524,868 B2 | 1/2020 | Cooper et al. |
| 10,537,331 B2 | 1/2020 | Scirica et al. |
| 10,542,993 B2 | 1/2020 | Guerrera et al. |
| 10,548,598 B2 | 2/2020 | Prescott et al. |
| 10,561,424 B2 | 2/2020 | Penna et al. |
| 10,568,631 B2 | 2/2020 | Rebuffat et al. |
| 10,575,847 B2 | 3/2020 | Hessler et al. |
| 10,595,871 B2 | 3/2020 | Racenet et al. |
| 10,595,872 B2 | 3/2020 | Milliman |
| 10,603,042 B2 | 3/2020 | Sgroi |
| 10,624,646 B2 | 4/2020 | Bae et al. |
| 10,639,041 B2 | 5/2020 | Williams |
| 10,653,414 B2 | 5/2020 | Williams |
| 10,898,196 B2 | 1/2021 | Sapienza et al. |
| 11,419,624 B2 * | 8/2022 | Borek ................ A61B 17/1155 |
| 2002/0020732 A1 * | 2/2002 | Adams ................ A61B 17/072 |
| | | 227/19 |
| 2003/0018236 A1 * | 1/2003 | Adams ................ A61B 90/30 |
| | | 600/128 |
| 2003/0111507 A1 | 6/2003 | Nunez |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0163598 A1 | 7/2010 | Belzer |
| 2010/0224668 A1 | 9/2010 | Fontayne et al. |
| 2010/0230465 A1 | 9/2010 | Smith et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0060258 A1 | 3/2013 | Giacomantonio |
| 2013/0105544 A1 | 5/2013 | Mozdzierz et al. |
| 2013/0105551 A1 | 5/2013 | Zingman |
| 2013/0126580 A1 | 5/2013 | Smith et al. |
| 2013/0153631 A1 | 6/2013 | Vasudevan et al. |
| 2013/0175315 A1 | 7/2013 | Milliman |
| 2013/0175318 A1 | 7/2013 | Felder et al. |
| 2013/0181035 A1 | 7/2013 | Milliman |
| 2013/0181036 A1 | 7/2013 | Olson et al. |
| 2013/0193190 A1 | 8/2013 | Carter et al. |
| 2013/0200131 A1 | 8/2013 | Racenet et al. |
| 2013/0206816 A1 | 8/2013 | Penna |
| 2013/0240597 A1 | 9/2013 | Milliman et al. |
| 2013/0277411 A1 | 10/2013 | Hodgkinson et al. |
| 2013/0284792 A1 | 10/2013 | Ma |
| 2014/0008413 A1 | 1/2014 | Williams |
| 2014/0046352 A1 | 2/2014 | Reboa et al. |
| 2014/0054356 A1 | 2/2014 | Hartwick et al. |
| 2014/0158747 A1 | 6/2014 | Measamer et al. |
| 2014/0284370 A1 | 9/2014 | Sahin |
| 2015/0083772 A1 | 3/2015 | Miller et al. |

(56) References Cited

U.S. PATENT DOCUMENTS

| | | |
|---|---|---|
| 2015/0173763 A1 | 6/2015 | Liu |
| 2015/0209045 A1 | 7/2015 | Hodgkinson et al. |
| 2017/0020528 A1 | 1/2017 | Racenet et al. |

FOREIGN PATENT DOCUMENTS

| | | |
|---|---|---|
| CN | 104039244 A | 9/2014 |
| CN | 104042288 A | 9/2014 |
| CN | 104367360 A | 2/2015 |
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 1671597 A1 | 6/2006 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 3023077 A1 | 5/2016 |
| EP | 3409217 A1 | 12/2018 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 02080781 A2 | 10/2002 |
| WO | 2004047654 A2 | 6/2004 |
| WO | 2008107918 A1 | 9/2008 |

OTHER PUBLICATIONS

European Examination Report from Appl. No. 14181908.6 dated May 3, 2016.
International Search Report and Written Opinion issued in corresponding International Application No. PCT/IB2022/054444 dated Aug. 9, 2022, 14 pages.

\* cited by examiner

DEVICES AND METHODS FOR SHORTENING A RECTAL STUMP DURING A LOWER ANTERIOR RESECTION PROCEDURE

FIELD

The disclosure relates generally to devices and methods for forming an anastomosis after removing sections of diseased tissue from tubular organs, and more specifically, to devices and methods for shortening a rectal stump prior to forming an anastomosis during a lower anterior resection procedure.

BACKGROUND

Devices for performing lower anterior resection (LAR) procedures to treat rectal cancer are known. During LAR procedures, diseased portions of the rectum are removed and the healthy portion of the rectum is reconnected to the colon. Circular stapling devices for forming an end-to-end anastomosis are known. Typically, a section the colon is secured to an anvil assembly of the circular stapling device, and a section of the rectal stump is secured about a loading unit of the circular stapling device. The rectal stump is typically shortened as much as possible. Shortening the rectal stump to a desired length using traditional methods require additional devices that may be bulky or otherwise difficult to operate.

Therefore, it would be beneficial to have a circular stapling device configured for shortening a rectal stump prior to forming an anastomosis.

SUMMARY

A loading unit for a circular stapling device includes a shell member, a staple pusher assembly operably disposed within the shell member, a knife pusher assembly operably disposed within the shell member, a trocar assembly operably disposed within the shell member, and a tissue retraction assembly disposed within the shell member between the knife pusher assembly and the trocar assembly. The shell member includes an elongate tubular portion. The trocar assembly includes a trocar member movable from an advance position and a retracted position. The tissue retraction assembly includes a tissue retractor.

In certain aspects of the disclosure, the elongate tubular portion of the shell member is six to twelve inches in length. The elongate tubular portion may include inner and outer portions and defines a cavity between the inner and outer portions. The staple pusher assembly and the knife pusher assembly may be operably received within the cavity and may be movable between advanced and retracted positions.

In other aspects of the disclosure, the tissue retraction assembly includes a holder. The holder may define a longitudinal opening and may be selectively movable along the inner portion of the shell member. The tissue retractor may extend through the longitudinal opening in the holder. The tissue retractor may be longitudinally fixed relative to the holder.

A circular stapler includes an adapter assembly configured for operable connection to an actuation assembly and a loading unit. The includes a shell member, a staple pusher assembly operably disposed within the shell member, a knife pusher assembly operably disposed within the shell member, a trocar assembly operably disposed within the shell member, and a tissue retraction assembly disposed within the shell member between the knife pusher assembly and the trocar assembly. The shell member includes an elongate tubular portion. The trocar assembly includes a trocar member movable from an advance position and a retracted position. The tissue retraction assembly includes a tissue retractor.

In certain aspects of the disclosure, the elongate tubular portion of the shell member is six to twelve inches in length. The elongate tubular portion may include inner and outer portions and defines a cavity between the inner and outer portions. The staple pusher assembly and the knife pusher assembly may be operably received within the cavity and may be movable between advanced and retracted positions.

In other aspects of the disclosure, the tissue retraction assembly includes a holder. The holder may define a longitudinal opening and may be selectively movable along the inner portion of the shell member. The tissue retractor may extend through the longitudinal opening in the holder. The tissue retractor may be longitudinally fixed relative to the holder.

A method of forming an anastomosis includes receiving a loading unit within a rectal stump of a patient, advancing a tissue retractor from the loading unit, securing the tissue retractor to the rectal stump, retracting the tissue retractor within the loading unit such that the rectal stump is drawn within the loading unit to shorten the rectal and stump, clamping, stapling and cutting the rectal stump.

In certain aspects of the disclosure, securing the tissue retractor to the rectal stump includes stitching the rectal stump to the tissue retractor. Advancing the tissue retractor from the loading unit may also include advancing a holder. Retracting the tissue retractor includes retracting the holder. The method may further include positioning a staple cartridge of the loading unit adjacent an anus of the patient as the rectal stump is drawn within the loading unit. The method may also include securing a colon to an anvil assembly and securing the anvil assembly relative to the loading unit.

BRIEF DESCRIPTION OF THE DRAWINGS

Aspects of the disclosed devices and methods for shortening rectal stumps during a lower anterior resection procedure are described herein with reference to the drawings, wherein.

DETAILED DESCRIPTION OF THE DRAWINGS

Figure 1:
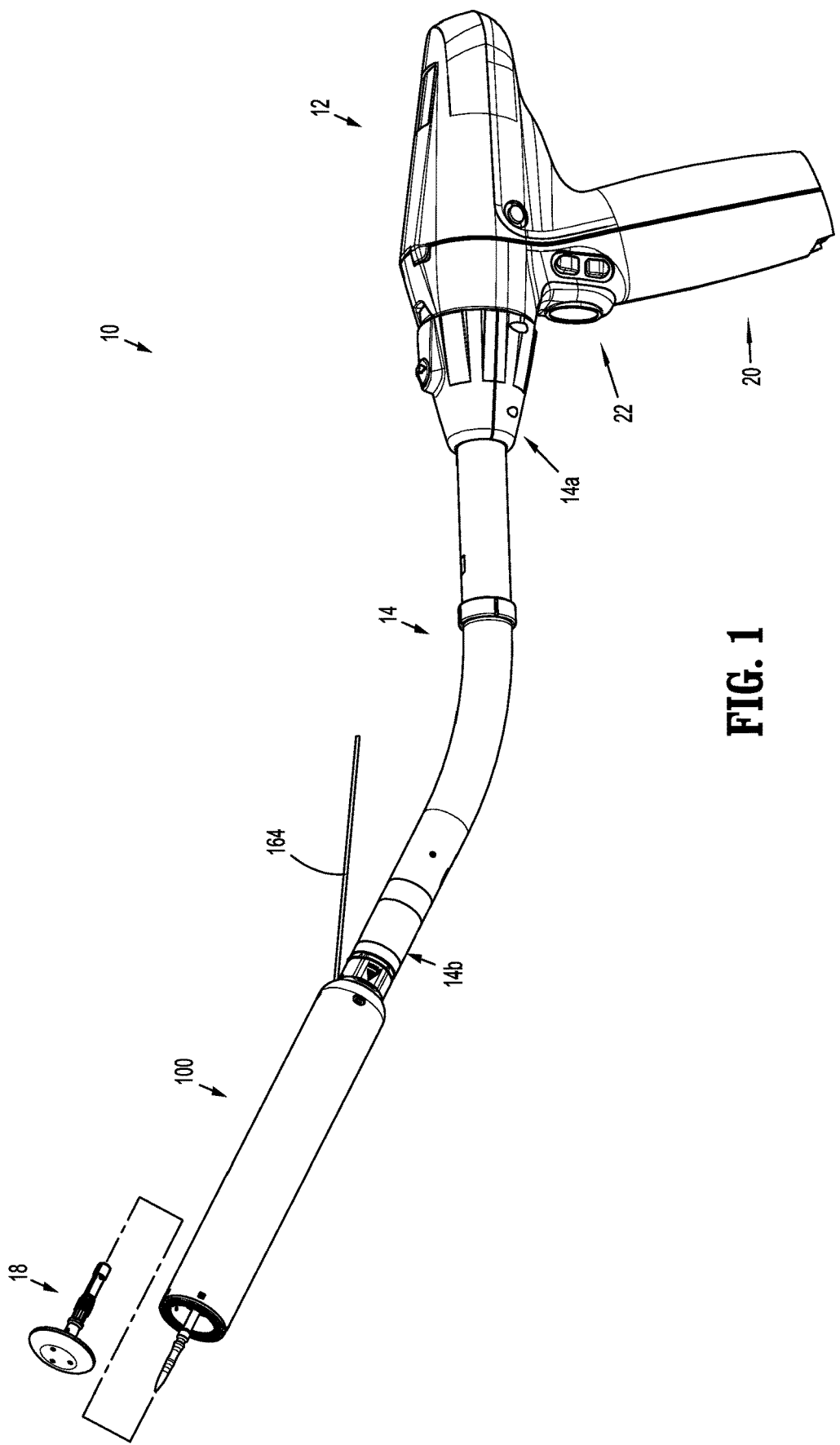
FIG. 1 is a perspective side view of a circular stapling apparatus according to aspects of the disclosure.

The disclosed devices and methods will now be described in detail with reference to the drawings in which like reference numerals designate identical or corresponding elements in each of the several views. However, it is to be understood that the aspects of the disclosure provided herein are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

In this description, the term "proximal" is used generally to refer to that portion of the device that is closer to a clinician, while the term "distal" is used generally to refer to that portion of the device that is farther from the clinician. In addition, the term "endoscopic" is used generally used to refer to endoscopic, laparoscopic, arthroscopic, and/or any other procedure conducted through small diameter incision or cannula. Further, the term "clinician" is used generally to refer to medical personnel including doctors, nurses, and support personnel. As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

Figure 2:
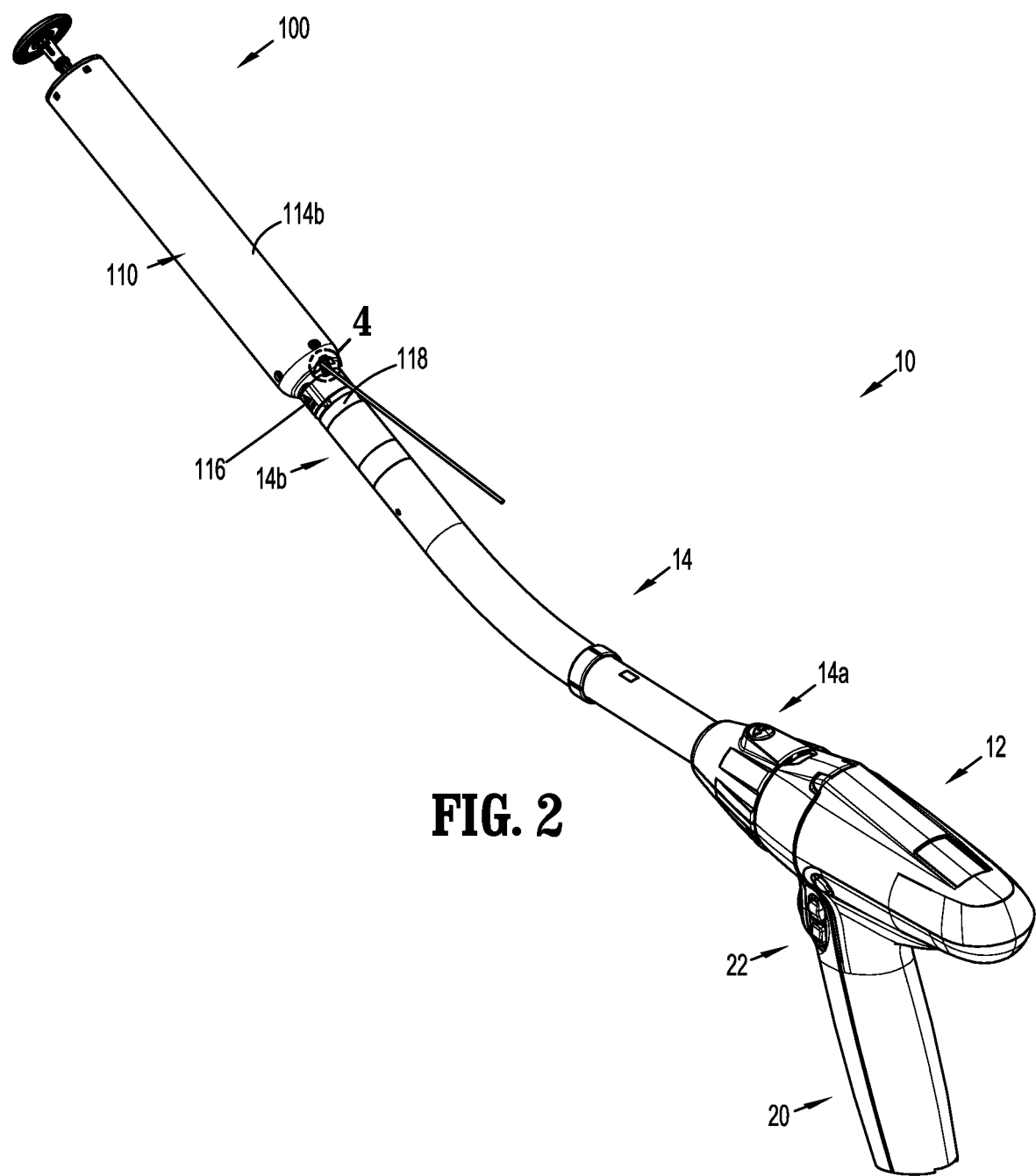
FIG. 2 is a perspective end view of the circular stapling apparatus shown in FIG. 1.

FIGS. 1 and 2 illustrate a circular stapling device shown generally as circular stapler 10, including a circular loading unit shown generally as loading unit 100. The circular stapler 10 includes a handle assembly 12, an adapter assembly or elongate body 14, the loading unit 100, and an anvil assembly 18 supportable for movement in relation to the loading unit 100 between spaced (FIG. 12) and approximated (FIG. 13) or clamped positions, as is known in the art. A proximal portion 14a of the adapter assembly 14 is releasably coupled to the handle assembly 12, and the loading unit 100 is releasably coupled to a distal portion 14b of the adapter assembly 14. The handle assembly 12 includes a stationary grip 20 that supports actuation buttons 22 for controlling operation of various functions of the circular stapler 10 including approximation of the loading unit 100 and anvil assembly 18, firing of staples from the circular reload 100, and cutting or coring of tissue (not shown) clamped between the loading unit 100 and the anvil assembly 18. Although the handle assembly 12, adapter assembly 14, and loading unit 100 are shown as separate components that are releasably coupled to one another, it is envisioned that any one or all of the components may be integrally formed.

The circular stapler 10 is illustrated as an electrically powered stapling device including an electrically powered handle assembly 12 that may support one or more batteries (not shown). The elongate body 14 is in the form of an adapter assembly that translates power from the handle assembly 12 to the loading unit 100 and anvil assembly 18. Examples of electrically powered stapling devices can be found in U.S. Pat. Nos. 9,055,943, 9,023,014, and U.S. Publication Nos. 2018/0125495 ("the '495 Publication"), and 2017/0340351, the entire contents of which are incorporated by reference herein in their entireties. Although shown and disclosed as relating to a powered handle assembly, it is envisioned that the aspects of the disclosure may be incorporated into manually operated stapling devices. For exemplary manually actuated stapling devices, please refer to U.S. Pat. Nos. 7,364,060, and 7,303,106. It is also envisioned that the aspects of the disclosure may be incorporated into robotically controlled stapling devices.

Figure 3:
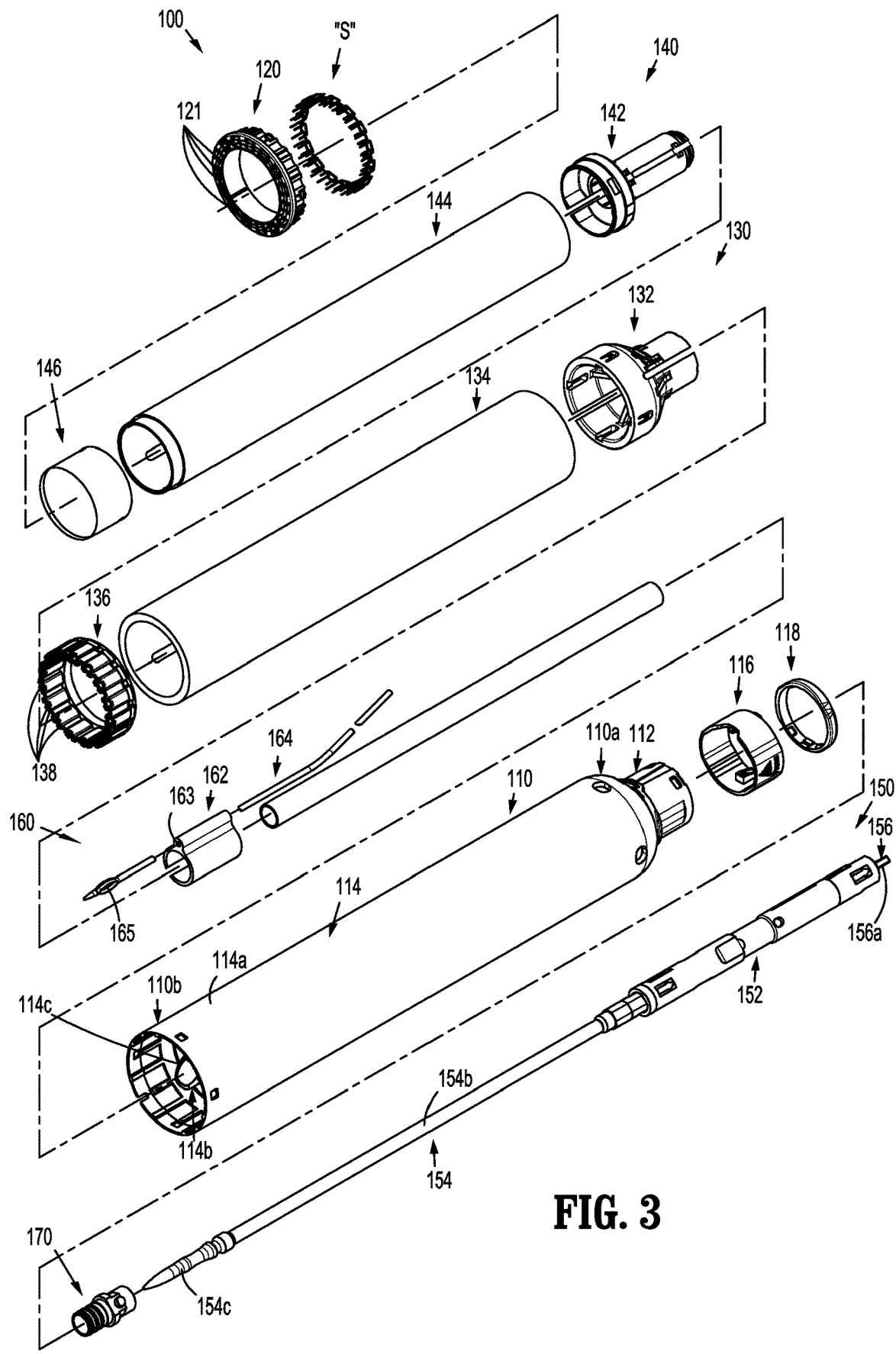
FIG. 3 is a perspective side view of a loading unit of the circular stapling apparatus shown in FIGS. 1 and 2, with parts separated.

FIG. 3 illustrates the loading unit 100 of the circular stapler 10 which includes a shell member or housing 110, a staple cartridge 120 for supporting a plurality of staples "S", a staple pusher assembly 130, a knife pusher assembly 140 positionable radially inward of the staple pusher assembly 130, a trocar assembly 150 positionable radially inward of the knife pusher assembly 140, and a tissue retraction assembly 160 positionable between the trocar assembly 150 and the knife pusher assembly 140. As will become apparent from the following disclosure, loading unit 100 is structurally and functional similar to known loading units, and therefore only the difference therebetween will be described in detail. For a detailed description of exemplary loading units, please refer to the '495 Publication.

Figure 4:
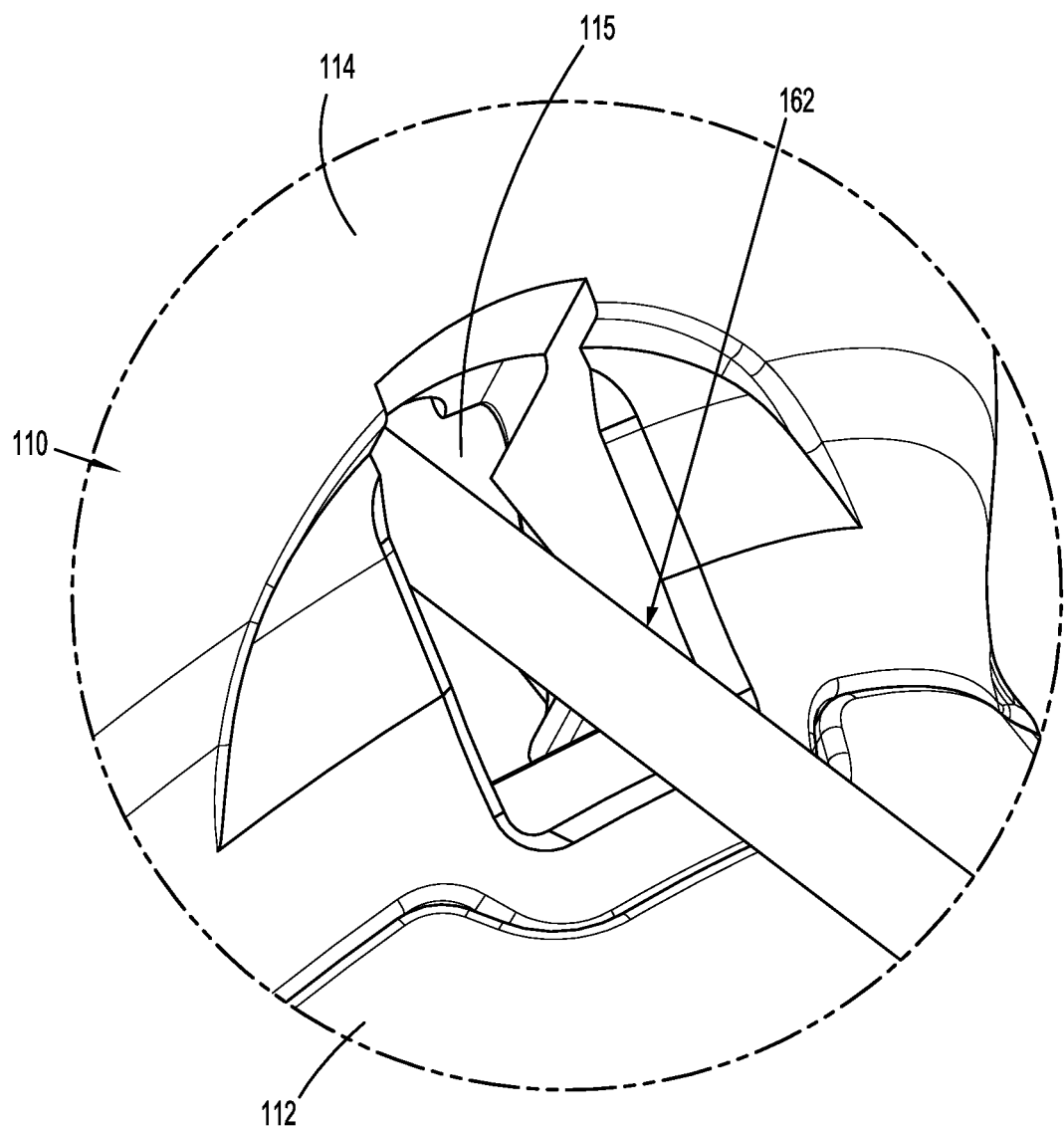
FIG. 4 is an enlarged view of the indicated area of detail shown in FIG. 2.
Figure 9:
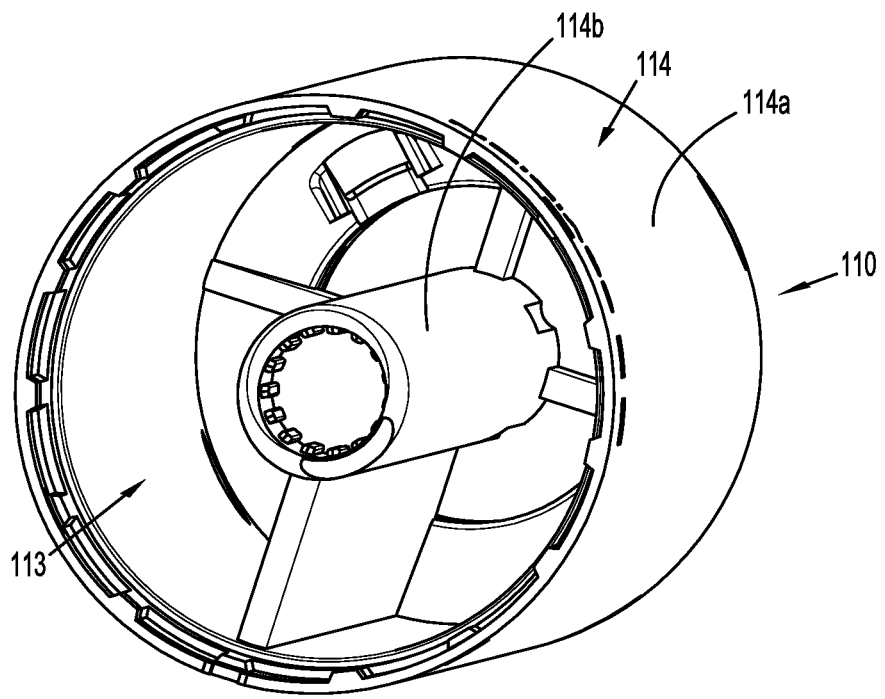
FIG. 9 is a perspective end view of a shell member of the loading unit shown in FIG. 3.

The shell member 110 of the loading unit 100 includes a connector portion 112 on a proximal portion 110a for operable connection to the adapter assembly 14 and a tubular portion 114 extending from the connector portion 112. The connector portion 112 supports a locking sleeve 116 and a locking ring 118. Although shown including the locking sleeve 116 and the locking ring 118, it is envisioned that the loading unit 100 may be releasably secured to the adapter assembly 14 in any suitable manner. The tubular portion 114 of the shell member 110 includes an outer housing portion 114a and an inner housing portion 114b spaced from the outer housing portion 112 to define an annular cavity 113 (FIG. 9). The annular cavity 113 is configured to operably receive the staple pusher assembly 130, the knife pusher assembly 140, and the tissue retraction assembly 160. The inner housing portion 114b is configured to operably receive the trocar assembly 140 and includes a tapered distal end 114c. The shell member 110 of the loading unit 100 defines an opening 115 (FIG. 4), disposed between the connector portion 112 and the tubular portion 114, and in fluid communication with the annular cavity 113. A distal portion 110b of the shell member 110 is configured to support the staple cartridge 120. The shell member 110 includes a length sufficient to accommodate shortening of the rectal stump as described below. The shell member 110 may be from about two to about six times longer than a shell member of a traditional circular stapling loading unit. It is envisioned that the shell member 110 may be anywhere from three inches (3") to ten inches (10") in length.

The staple cartridge 120 of the loading unit 100 is supportable on the distal portion 110b of the shell member 110 and defines annular rows of staple pockets 121. Each of the staple pockets 121 supports one of the plurality of staples "S". Although shown including three rows of staple pockets 121, it is envisioned that the staple cartridge 120 may support any number of annular of staples "S" in any suitable configuration.

The staple pusher assembly 130 of the loading unit 100 includes a staple pusher base 132, a staple pusher extension 134, and a staple pusher member 136. The staple pusher assembly 130 is movable within the annular cavity 113 (FIG. 4) of the shell member 110 between a retracted position (FIG. 5) and an advanced position (FIG. 13), to eject the staples "S" from the staple cartridge 120. The staple pusher member 136 of the staple pusher assembly 130 includes a plurality of fingers 138 corresponding to the staple pockets 121 of the staple cartridge 120. The plurality of fingers 138 are movable through the respective staple pockets 121 to eject the staples "S" from the staple pockets 121 when the staple pusher assembly 130 is moved from the retracted position (FIG. 5) to the advanced position (FIG. 13) within the shell member 110. The staple pusher extension 134 includes a length configured to accommodate the increased length of the shell member 110. A detailed description of the structure and function of exemplary staple pusher assemblies is provided in the '495 Publication, the content of which was previously incorporated by reference herein in its entirety.

The knife pusher assembly 140 of the loading unit 100 includes a knife pusher base 142, a knife pusher extension 144, and an annular knife 146. The knife assembly 140 is movable within the annular cavity 113 (FIG. 4) of the shell member 110 between a retracted position (FIG. 5) and an advanced position (FIG. 13) to cut the tissue. The knife pusher assembly 140 is advanceable independent of the advancement of the staple pusher assembly 130, although simultaneous advancement is envisioned. The knife pusher extension 144 includes a length configured to accommodate the increased length of the shell member 110. A detailed description of the structure and function of exemplary knife pusher assemblies is provided in the '495 Publication.

The trocar assembly 150 of the loading unit 100 includes a trocar housing 152, a trocar member 154 extending from the trocar housing 152, and a drive member 156 rotatable supported within the trocar housing 152. A sleeve 158 is receivable about the trocar member 154 and is configured to reduce friction between the trocar member 154 and the inner wall 114b of the shell member 110. The trocar housing 152 of the trocar assembly 150 is configured to be releasably secured within the distal portion 14b of the adapter assembly 14 (FIG. 1) of the circular stapler 10, to permit sterilization and reuse of the trocar assembly 150. Alternatively, the trocar assembly 150 is integrally formed with the adapter assembly 14.

The trocar member 154 of the trocar assembly 150 includes an internally threaded proximal portion 154a (FIG. 5), an elongate central portion 154b, and a sharpened distal portion 154c. The proximal, central, and distal portions 154a, 154b, 154c may be integrally formed and/or formed as separate components that are secured together in any suitable manner. The drive member 156 of the trocar assembly 150 includes a proximal portion 156a configured to engage a rotary drive member (not shown) extending through the adapter assembly 14 and a threaded distal portion 156b for engaging the internally threaded proximal portion 154a of the trocar member 154. Rotation of the drive member 156 in a first direction causes advancement of the trocar member 154 relative to the trocar housing 154, and rotation of the drive member 156 in a second direction causes retraction of the trocar member 154 relative to the trocar housing 152. The elongate central portion 154b of the trocar member 154 includes a length configured to accommodate the increased length of the shell member 110. A detailed description of the structure and function of exemplary trocar assemblies is provided in the '495 Publication.

The tissue retraction assembly 160 of the loading unit 100 includes a holder or guide 162 and a tissue retractor 164 extending through the holder 162. The holder 162 is configured to be received about the inner housing portion 114b of the tubular portion 114 of the shell member 110. As will be described in further detail below, the holder 162 of the tissue retraction assembly 160 is configured to slide along the inner housing portion 114a of the shell assembly 110 during tissue retraction. The holder 162 defines a longitudinal opening 163 for receiving a distal portion of the tissue retractor 164. The tissue retractor 164 includes a piercing distal tip 164b and defines an eye 165 along the distal portion thereof.

The loading unit 100 includes a bushing 170 positionable within the connector portion 112 of the shell member 110 to ensure the connection between the staple pusher base 132 of the staple pusher assembly 130 and a staple driver (not shown) and between the knife pusher base 142 of the knife pusher assembly 140 and a knife drive (not shown).

Figure 5:
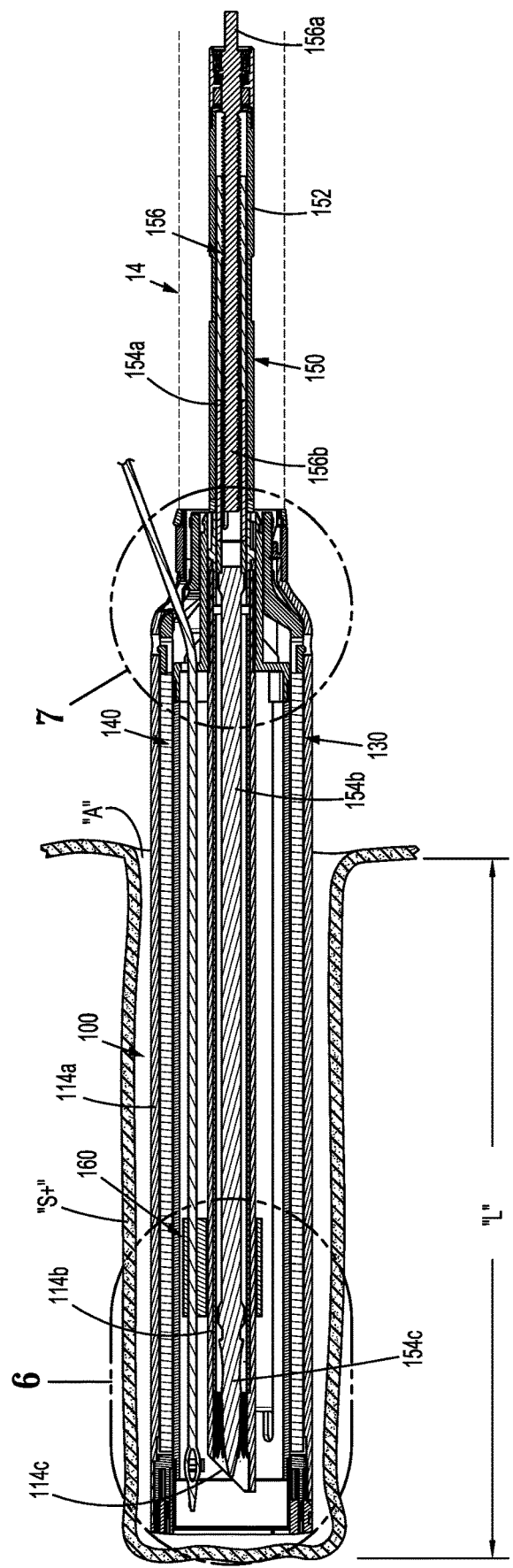
FIG. 5 is a cross-sectional side view the loading unit shown in FIG. 3 received within a rectal stump of a patient.
Figure 7:
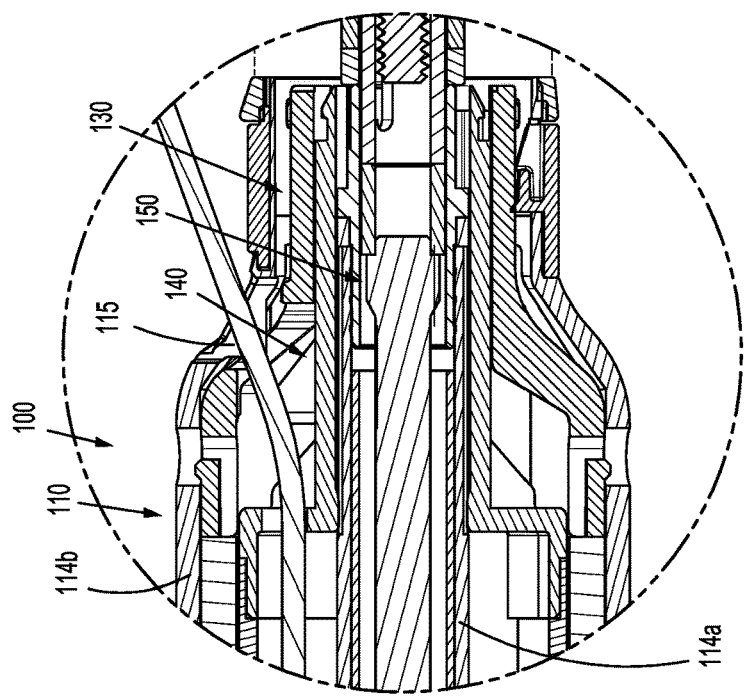
FIG. 7 is an enlarged view of the indicated area of detail shown in FIG. 5.
Figure 6:
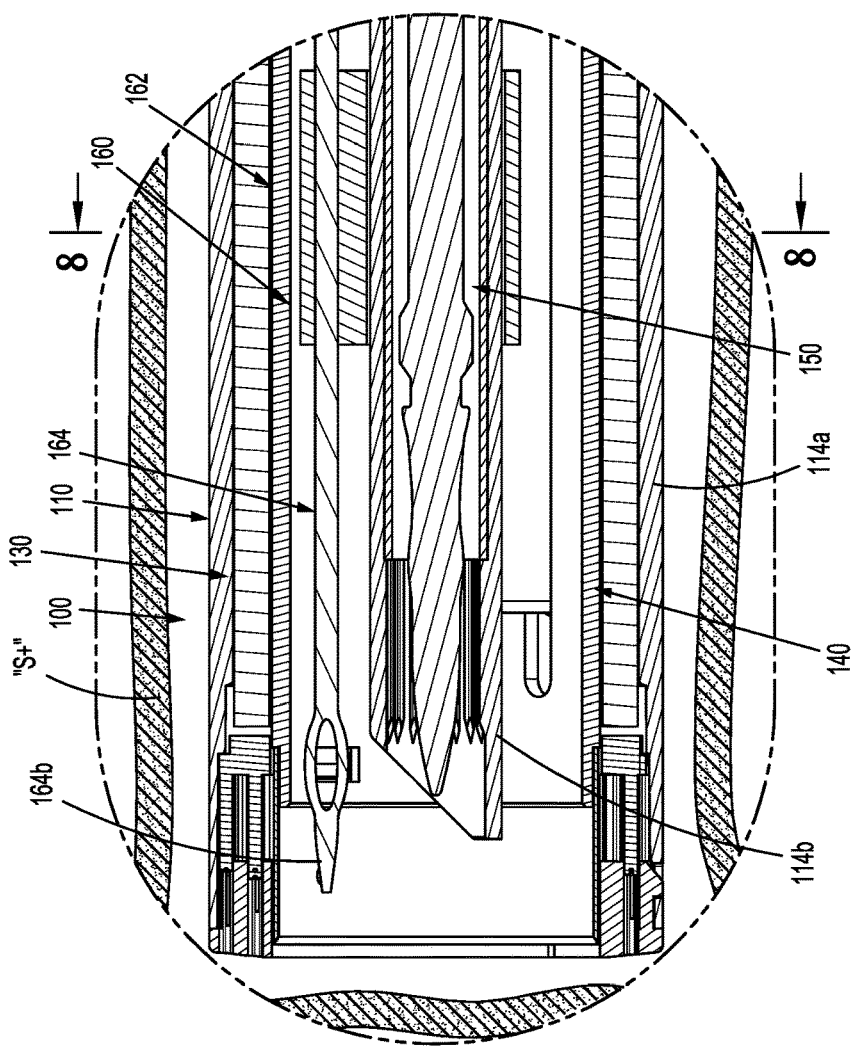
FIG. 6 is an enlarged view of the indicated area of detail shown in FIG. 5.
Figure 8:
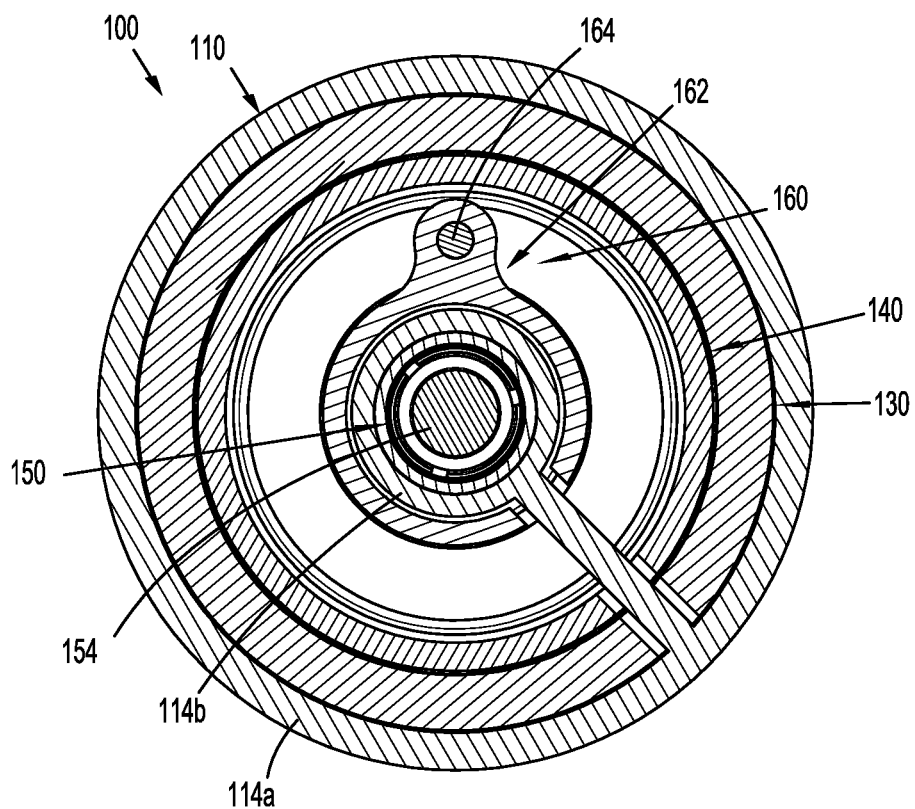
FIG. 8 is cross-sectional end view of taken along lines 8-8 shown in FIG. 6.

A method of performing an anastomosis procedure, including shortening of the rectal stump, during a lower anterior resection (LAR) procedure utilizing the loading unit 100 will be described in detail with reference to FIGS. 5-15. Initially, using conventional means, the clinician removes a diseased section of a tubular organ leaving a rectal stump "St" (FIG. 5). The rectal stump "St" may include any length "L", and does not require shortening prior to use of the circular stapler 10 (FIG. 1).

FIGS. 5-8 illustrates the loading unit 100 of the circular stapler 10 received through an anus "A" and within a rectal stump "St" a patient during an LAR procedure. The loading unit 100 is configured such that the proximal portion of the shell member 110 remains external of the anus "A" while the cartridge assembly 120 on the distal portion of the shell member 110 is positioned adjacent a distal portion of the rectal stump "St". In this manner, the tissue retractor 164 of the tissue retraction assembly 160 remains accessible to the clinician.

Prior to introducing the loading unit 100 through the anus "A" and into the rectal stump "St" of the patient, each of the stapler pusher assembly 130, the knife pusher assembly 140, the trocar member 154 of the trocar assembly 150, and the tissue retraction assembly 160 of the loading unit 100 is in their retracted positions. More particularly, the staple pusher assembly 130 and the knife pusher assembly 140 are in their proximal-most positions within the shell member 110, and the trocar member 154 is retained entirely with inner housing portion 114b of the shell member 110. The tissue retraction assembly 160 is positioned in the cavity 113 between the knife pusher assembly 130 and the inner housing portion 114b. The holder 162 of the tissue retraction assembly 160 is in its distal-most position about the inner housing portion 114b of the shell member 110 and the piercing distal tip 164b of the tissue retractor 164 of the tissue retraction assembly 160 is spaced from the staple cartridge 120.

Figure 10:
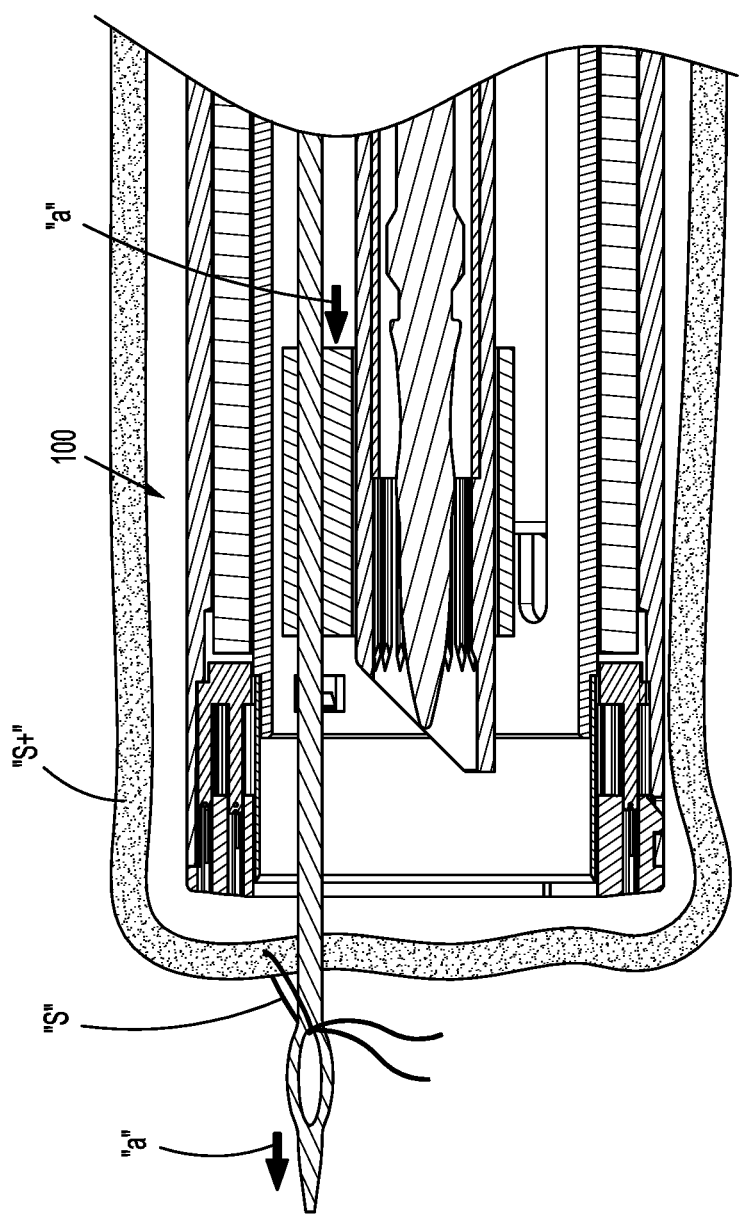
FIG. 10 is a cross-sectional side view of a distal portion of the loading unit shown in FIG. 3, with a tissue retractor of the loading unit in an advanced position and secured to the rectal stump.

FIG. 10 illustrates securing the rectal stump "St" to the tissue retractor 164 of the tissue retraction assembly 160. More particularly, the tissue retractor 164 is moved distal, e.g., advanced, as indicated by arrows "a", such that the piercing distal tip 164b of the tissue retractor 164 pierces the rectal stump "St". The tissue retractor 164 is advanced until the eye 165 of the tissue retractor 164 is positioned adjacent a distal portion of the rectal stump "St". The rectal stump "St" is then secured to the tissue retractor 164 in any suitable manner. As shown, the rectal stump "St" is secured to the tissue retractor 164 using a suture "s". It is envisioned that the tissue retractor may include a hook or other grasping mechanism for securing the rectal stump "St" to the tissue retractor 164. As shown, tissue retractor 164 of the tissue retraction assembly 160 is longitudinally fixed relative to the holder 162. In this manner, advancement of the tissue retractor 164 causes advancement of the holder 162 and retraction of the tissue retractor 164 causes retraction of the holder 162. It is envisioned that the tissue retractor 164 may move independent of the holder 162.

Figure 11:
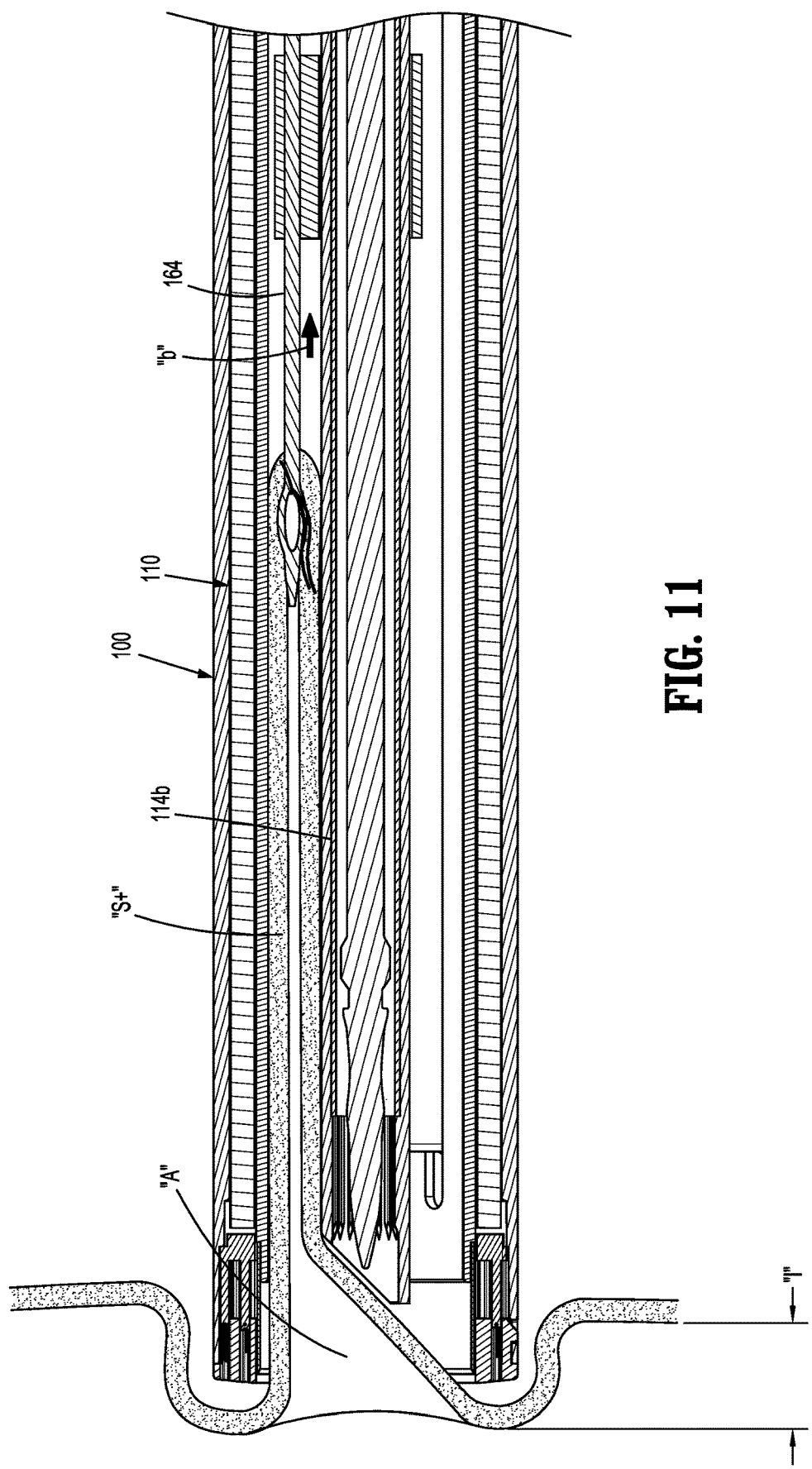
FIG. 11 is a cross-sectional side view of the loading unit shown in FIG. 10, with the tissue retractor in a retracted position.

FIG. 11 illustrates the rectal stump "St" of the patient being retracted, or more particularly, invaginated, within the loading unit 100. More particularly, movement of the tissue retractor 164 in the proximal direction, e.g., retraction, as indicated by arrow "b", causes the rectal stump "St" to be retracted within the cavity 113 of the shell member 110 between the knife pusher extension 144 and annular knife 146 of the knife pusher assembly 140 and the inner housing portion 114b of the shell member 110. As noted above, because the tissue retractor 164 is longitudinally fixed relative to the holder 162, retraction of the tissue retractor 164 causes simultaneous retraction of the holder 162. The tissue retractor 164 is retracted relative to the shell member 110 unit the rectal stump "St" includes a length "l". The length "l" may include any length that the clinician determines most suited for the anastomosis procedure. The increased length of the shell member 110 accommodates a rectal stump "St" of any length.

As the rectal stump "St" is retracted within the shell member 110 of the loading unit 100, the loading unit 100 is gradually retracted through the anus "A" until the staple cartridge 120 on the distal end of the loading unit 100 is positioned adjacent the anus "A".

Figure 12:
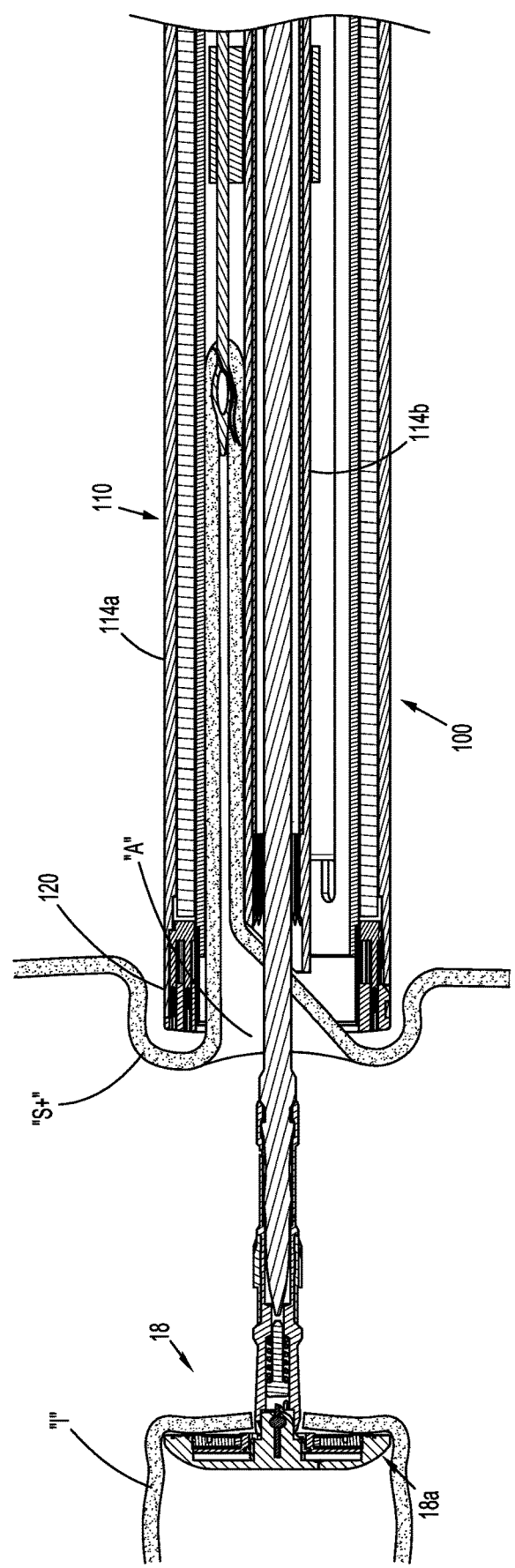
FIG. 12 is a cross-sectional side view of the loading unit shown in FIG. 11, with an anvil assembly secured to the trocar assembly of the loading unit.

FIG. 12 illustrates the anvil assembly 18 being secured to the trocar member 154 of the trocar assembly 150 of the loading unit 100. Prior to securing the anvil assembly 18 to the trocar member 154, a section of intestine "I" is secured about a head assembly 18a of the anvil assembly 18. Traditionally, tissue is secured to about the head assembly 18a of the anvil assembly 18 using a purse-string suture (not shown). The trocar member 154 is moved to a distal position to facilitate attachment of the anvil assembly 18 to the trocar member 154.

Figure 13:
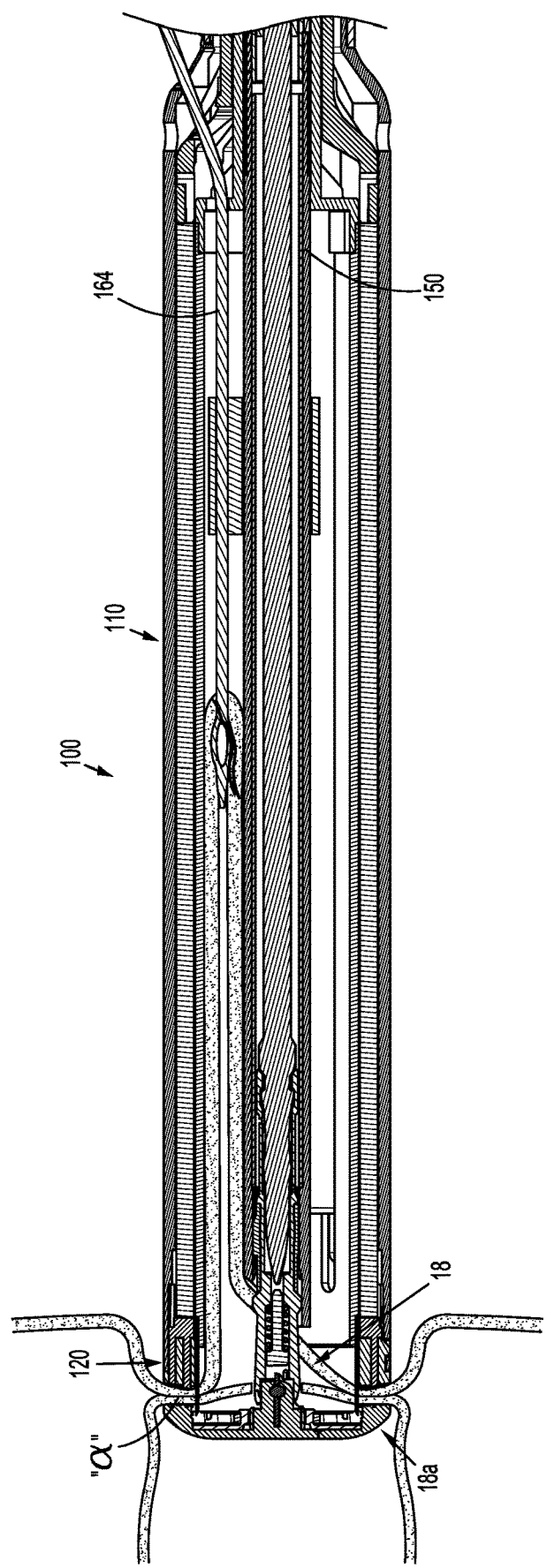
FIG. 13 is a cross-sectional side view of the loading unit shown in FIG. 12, with the anvil assembly in a clamped position and each of a staple pusher assembly and knife pusher assembly in advanced positions.

FIG. 13 illustrates the loading unit 100 during stapling and cutting of the rectal stump "St" and section of intestine "I" to form the anastomosis "a". More particularly, the staple pusher assembly 130 and the knife pusher assembly 140 are shown in their advanced positions. As noted previously, the staple pusher assembly 130 and the knife pusher assembly 140 may be advance independently or simultaneously. Prior to advancement of the staple pusher assembly 130, retraction of the trocar member 154 of the trocar assembly 150 approximates the anvil assembly 18 relative to the staple cartridge 120 to clamp the tissue of the rectal stump "St" and the section of intestine "I" between the head assembly 18a of the anvil assembly 18 and the staple cartridge 120 of the loading unit 100.

Figure 14:
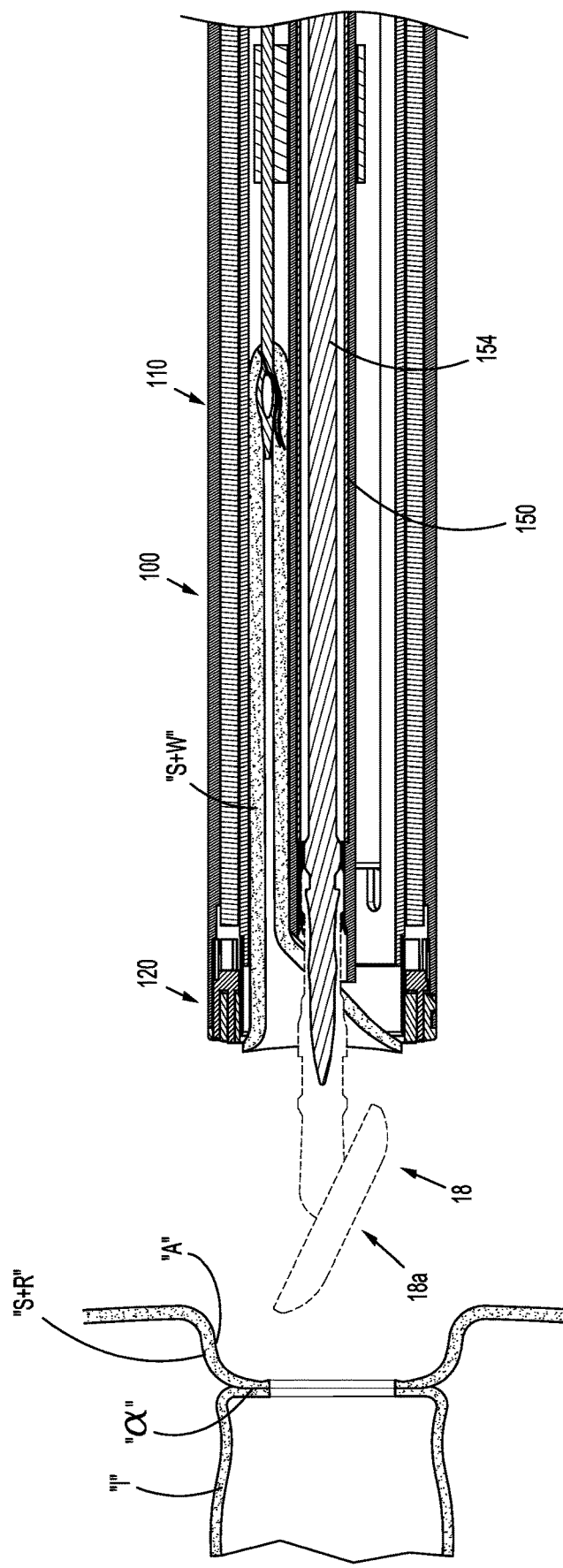
FIG. 14 is a cross-sectional side view of the loading unit shown in FIG. 13, subsequent to forming an anastomosis and after removal from the anus.

FIG. 14 illustrates the loading unit 100 subsequent to the forming of the anastomosis "a" and removal of the loading unit 100 from the anus "A" of the patient. To permit allow for tilting of the head assembly 18a of the anvil assembly 18, the anvil assembly 18 is first advanced relative to the loading unit 100 by advancing the trocar member 154 of the trocar assembly 100. Once the head assembly 18a of the anvil assembly 18 is move away from the staple cartridge 120 of the loading unit 100, the head assembly 18a pivots to the tilted position to permit removal of the anvil assembly 18 and loading unit 100 from the anus "A". A waste section of the rectal stump "StW" is removed with the loading unit 100 and disposed of in a traditional manner. A remaining section of the rectal stump "StR" is secured to the section of intestine "I" at the anastomosis "a".

It is envisioned that the loading unit may be configured for single use, e.g., disposable, or may be configured for sterilization and reuse. The loading units 100 are available in various lengths and diameters, and with various staple configurations.

Figure 15:
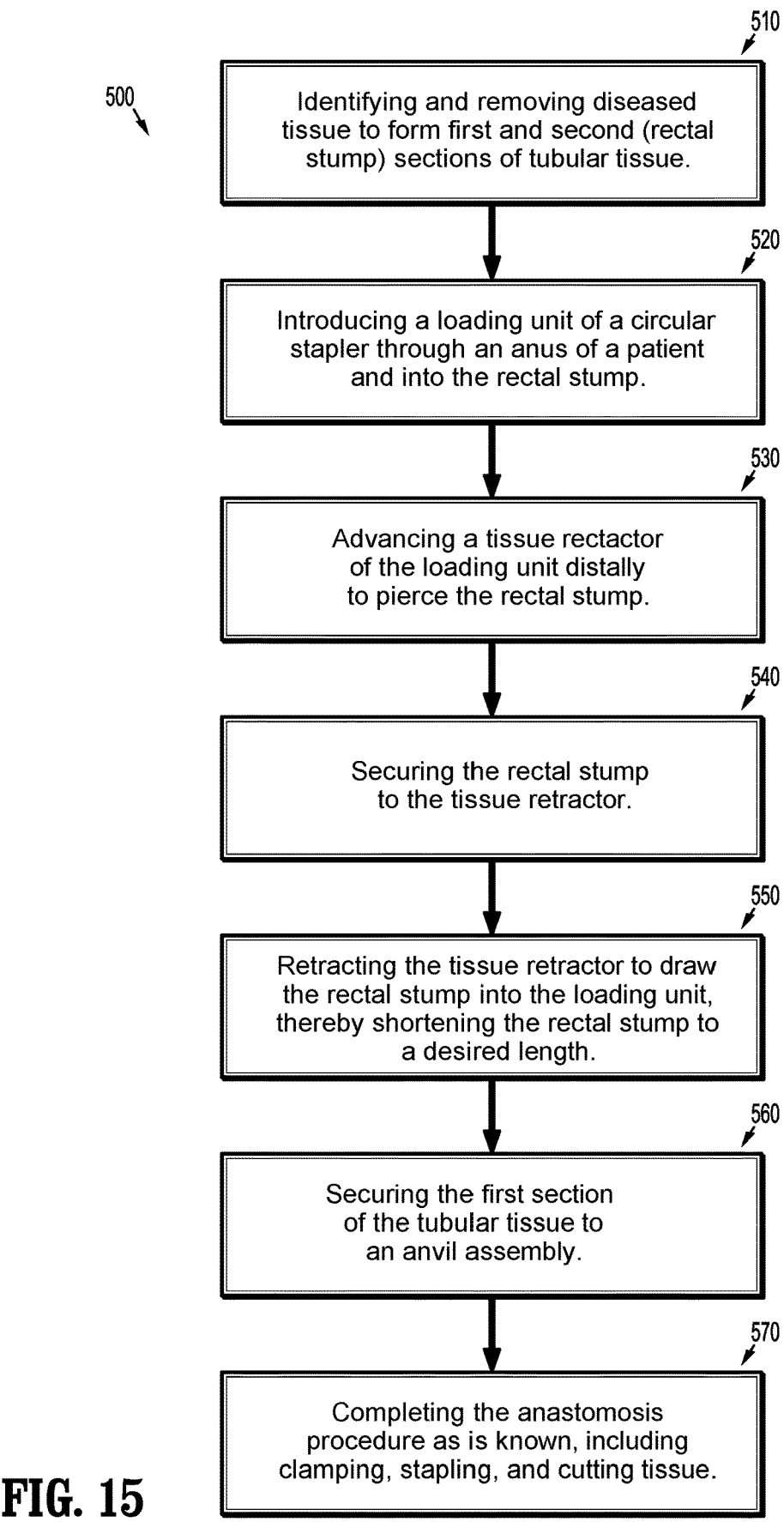
FIG. 15 is a flow chart of a method for forming an anastomosis during a lower anterior resection procedure.

FIG. 15 is a flow chart of the method of forming an anastomosis 500 including shortening of a rectal stump. In review, initially, the method includes identifying the diseased tissue and separating the diseased tissue from the surrounding healthy tissue 510. Next, the method includes introducing a loading unit of a circular stapler through the anus of a patient and into the rectal stump 520. The method then includes advancing a tissue retractor of the loading unit distally to pierce the rectal stump 530 and securing the rectal stump to the tissue retractor 540. Next, the method includes retracting the tissue retractor to draw the rectal stump into the loading unit, thereby shortening the rectal stump 550. At any time after forming the first and second sections of tubular tissue, the method includes securing the first section of the tissue to an anvil assembly 560. The method of then includes completing the anastomosis procedure 570, which entail securing the anvil assembly relative to the loading unit, clamping the tissue to be stapled, stapling the clamped tissue, and cutting the clamped tissue.

Persons skilled in the art will understand that the devices and methods specifically described herein and illustrated in the accompanying drawings are non-limiting exemplary aspects of the disclosure. It is envisioned that the elements and features illustrated or described in connection with one exemplary aspect of the disclosure may be combined with the elements and features of another without departing from the scope of the disclosure. As well, one skilled in the art will appreciate further features and advantages of the disclosure based on the above-described aspects of the disclosure. Accordingly, the disclosure is not to be limited by what has been particularly shown and described, except as indicated by the appended claims.

What is claimed is:

1. A loading unit for a circular stapling device, the loading unit comprising:
   a shell member having an elongate tubular portion;
   a staple pusher assembly operably disposed within the shell member;
   a knife pusher assembly operably disposed within the shell member;
   a trocar assembly operably disposed within the shell member and including a trocar member movable from an advance position and a retracted position; and
   a tissue retraction assembly disposed within the shell member between the knife pusher assembly and the trocar assembly, the tissue retraction assembly including a tissue retractor.

2. The loading unit of claim 1, wherein the elongate tubular portion of the shell member is six to twelve inches in length.

3. The loading unit of claim 1, wherein the elongate tubular portion includes inner and outer portions and defines a cavity between the inner and outer portions.

4. The loading unit of claim 3, wherein the tissue retraction assembly includes a holder, the holder defining a longitudinal opening and being selectively movable along the inner portion of the shell member.

5. The loading unit of claim 4, wherein the tissue retractor extends through the longitudinal opening in the holder.

6. The loading unit of claim 5, wherein the tissue retractor is longitudinally fixed relative to the holder.

7. The loading unit of claim 1, wherein the staple pusher assembly and the knife pusher assembly are operably received within the cavity and are movable between advanced and retracted positions.

8. A circular stapler comprising:
an adapter assembly configured for operable connection to an actuation assembly; and
a loading unit including:
a shell member having an elongate tubular portion;
a staple pusher assembly operably disposed within the shell member;
a knife pusher assembly operably disposed within the shell member;
a trocar assembly operably disposed within the shell member and including a trocar member movable from an advance position and a retracted position; and
a tissue retraction assembly disposed within the shell member between the knife pusher assembly and the trocar assembly, the tissue retraction assembly including a tissue retractor.

9. The circular stapler of claim 8, wherein the elongate tubular portion of the shell member is six to twelve inches in length.

10. The circular stapler of claim 8, wherein the elongate tubular portion includes inner and outer portions and defines a cavity between the inner and outer walls.

11. The circular stapler of claim 10, wherein the tissue retraction assembly includes a holder, the holder defining a longitudinal opening and being selectively movable along the inner portion of the shell member.

12. The circular stapler of claim 11, wherein the tissue retractor extends through the longitudinal opening in the holder.

13. The circular stapler of claim 12, wherein the tissue retractor is longitudinally fixed relative to the holder.

14. The circular stapler of claim 8, wherein the staple pusher assembly and the knife pusher assembly are operably received within the cavity and are movable between advanced and retracted positions.

15. A method of forming an anastomosis, the method comprising:
receiving a loading unit within a rectal stump of a patient;
advancing a tissue retractor from the loading unit;
securing the tissue retractor to the rectal stump by stitching the rectal stump to the tissue retractor;
retracting the tissue retractor within the loading unit such that the rectal stump is drawn within the loading unit to shorten the rectal stump; and
clamping, stapling and cutting the rectal stump.

16. The method of claim 15, wherein advancing the tissue retractor from the loading unit also includes advancing a holder.

17. The method of claim 16, wherein retracting the tissue retractor includes retracting the holder.

18. The method of claim 15, further including positioning a staple cartridge of the loading unit adjacent an anus of the patient as the rectal stump is drawn within the loading unit.

19. A method of forming an anastomosis, the method comprising:
receiving a loading unit within a rectal stump of a patient;
advancing a tissue retractor from the loading unit;
securing the tissue retractor to the rectal stump;
retracting the tissue retractor within the loading unit such that the rectal stump is drawn within the loading unit to shorten the rectal stump;
securing a colon to an anvil assembly and securing the anvil assembly relative to the loading unit; and
clamping, stapling and cutting the rectal stump.

\* \* \* \* \*